United States Patent
Bagaria

(10) Patent No.: US 6,686,167 B2
(45) Date of Patent: Feb. 3, 2004

(54) TEST DEVICE FOR DETECTING SEMEN AND METHOD OF USE

(76) Inventor: Padma S. Bagaria, P.O. Box 4040, West Hills, CA (US) 91308

(*) Notice: Subject to any disclaimer, the term of this patent is extended or adjusted under 35 U.S.C. 154(b) by 29 days.

(21) Appl. No.: 09/776,493

(22) Filed: Feb. 3, 2001

(65) Prior Publication Data

US 2002/0106696 A1 Aug. 8, 2002

(51) Int. Cl.[7] .................. G01N 33/543; G01N 33/53
(52) U.S. Cl. .................. 435/7.2; 422/55; 422/56; 422/57; 422/58; 435/7.92; 435/7.94; 435/287.2; 435/287.7; 435/287.9; 435/805; 435/810; 435/970; 436/63; 436/169; 436/513; 436/514; 436/518; 436/530; 436/805; 436/810
(58) Field of Search ............... 435/7.2, 7.92, 435/7.94, 287.2, 287.7, 287.9, 805, 810, 970; 436/513, 518, 514, 530, 63, 169, 805, 810; 422/55, 56, 57, 58

(56) References Cited

U.S. PATENT DOCUMENTS 6,319,676 B1 * 11/2001 Nazareth et al. ............. 435/7.5

OTHER PUBLICATIONS

Graves et al, "Postcoital Detection of a Male–Specific Semen Protein", The New England Journal of Medicine, 1985, 312, pp. 338–343.*

* cited by examiner

Primary Examiner—Christopher L. Chin

(57) ABSTRACT

A test device (20) for detecting semen includes a strip (22) having an introduction station (24), a test station (26), and a control station (28) disposed in spaced apart relationship. The introduction station (24) has labeled p30 antibodies, the test station (26) has immobilized p30 antibodies, and the control station has immobilized polyclonal antibodies. A test sample (500) is deposited in the introduction station (24). If semen is present in the test sample (500), a colored line will appear at the test station (26) and at the control station (28). If no semen is present in the test sample (500), a colored line will only appear at the control station (28).

2 Claims, 5 Drawing Sheets

KEY

⚰ MONOCLONAL p30 ANTIBODIES

○ LABEL

⚰ LABELED MONOCLONAL p30 ANTIBODIES

🐚 p30 ANTIGEN

Y IMMOBILIZED MONOCLONAL p30 ANTIBODIES

↑ IMMOBILIZED POLYCLONAL ANTIBODIES

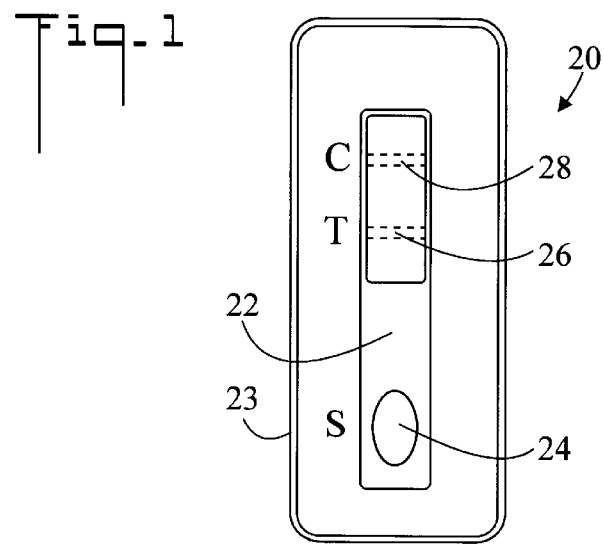
Fig_1
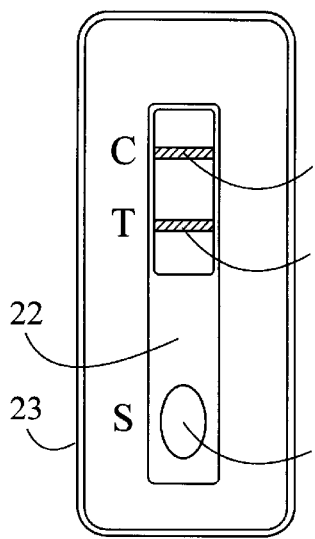
Fig_2
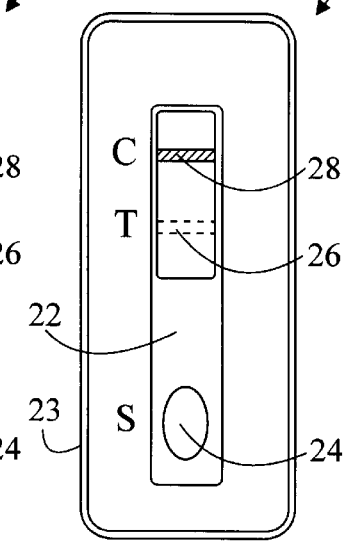
Fig_3
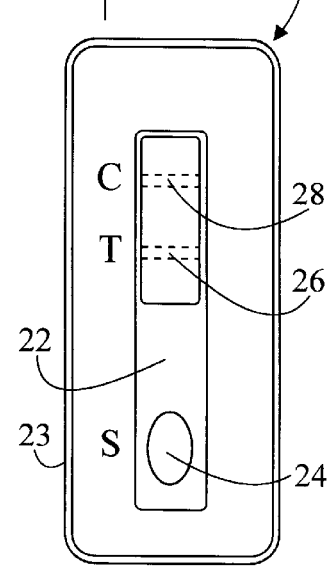
Fig_4

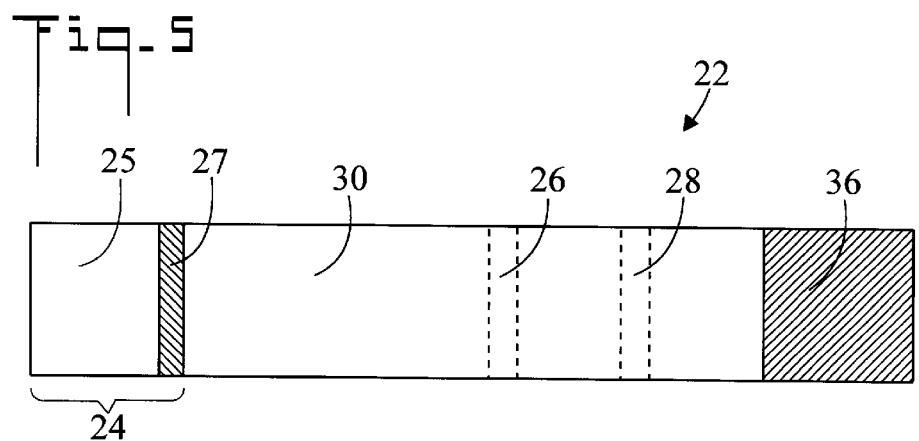
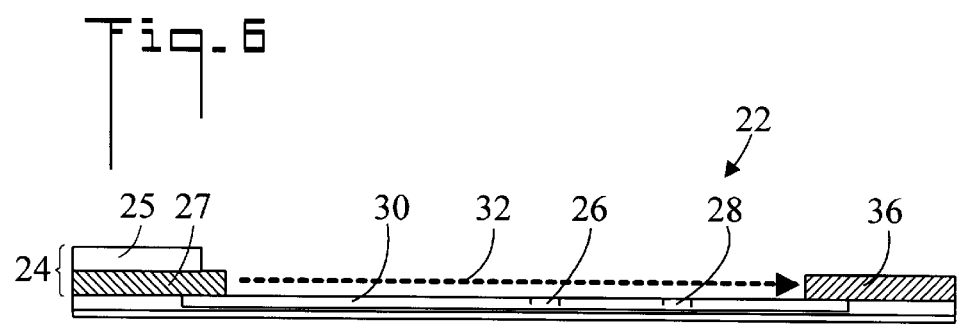

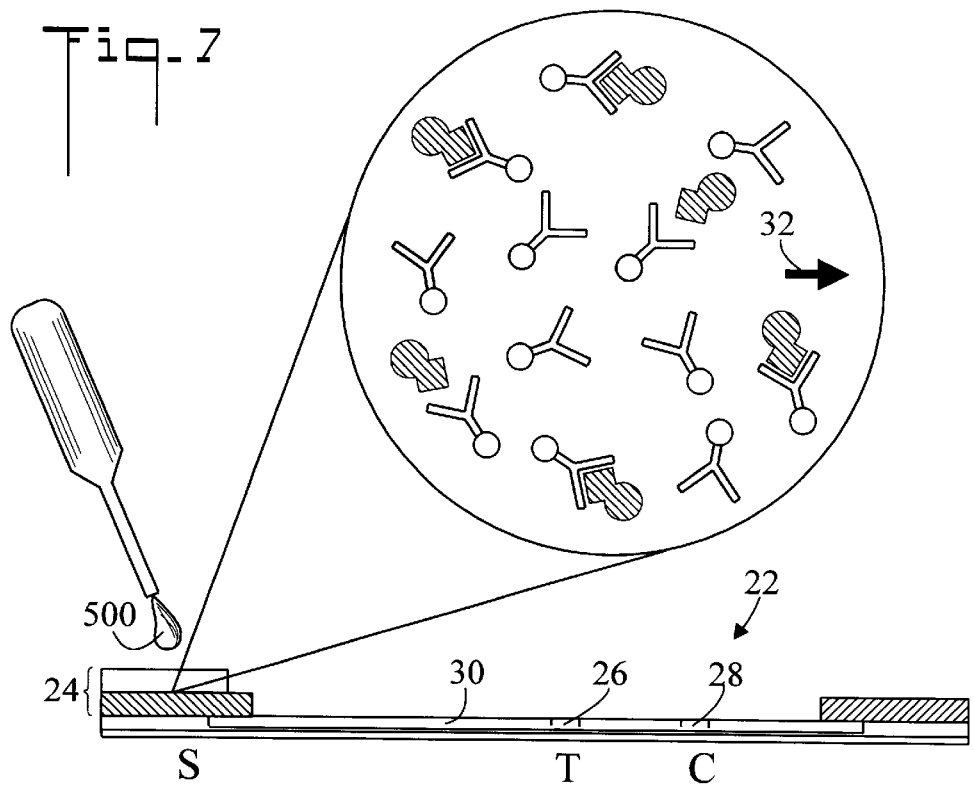
Fig. 7
KEY
 MONOCLONAL p30 ANTIBODIES
 LABEL
 LABELED MONOCLONAL p30 ANTIBODIES
 p30 ANTIGEN
 IMMOBILIZED MONOCLONAL p30 ANTIBODIES
 IMMOBILIZED POLYCLONAL ANTIBODIES

KEY

⅄ MONOCLONAL p30 ANTIBODIES

○ LABEL

⅄○ LABELED MONOCLONAL p30 ANTIBODIES p30 ANTIGEN

Y IMMOBILIZED MONOCLONAL p30 ANTIBODIES

⋃ IMMOBILIZED POLYCLONAL ANTIBODIES

KEY

⅄ MONOCLONAL p30 ANTIBODIES

○ LABEL

⅄ LABELED MONOCLONAL p30 ANTIBODIES p30 ANTIGEN

Y IMMOBILIZED MONOCLONAL p30 ANTIBODIES

IMMOBILIZED POLYCLONAL ANTIBODIES

US 6,686,167 B2

TEST DEVICE FOR DETECTING SEMEN AND METHOD OF USE

TECHNICAL FIELD

The present invention pertains generally to immunoassays for determining the presence of a particular analyte, and in particular, to a test device which may be used to detect the presence of semen.

BACKGROUND ART

Immunoassay test devices are well known in the art. These devices are employed to detect a wide variety of substances. For example, U.S. Pat. No. 4,313,734 shows a method, test kit, and labeled component for the detection and/or determination of one or more components of the reaction between a specific binding protein and the corresponding bindable substance, in which one or more labeled components are used, that are obtained by coupling particles of a dispersion of a metal, metal compound or polymer nuclei, coated with a metal or metal compound, having a particle size of at least 5 nm, directly or indirectly to the desired component of the reaction. During the reaction or after an adequate reaction time, the physical properties and/or the amount of the metal and/or the formed metal containing agglomerate, is/are determined in the test sample, or optionally after a separation of the bound and free metal labeled components in one of the derived fractions.

U.S. Pat. No. 4,376,110 illustrates "two-site" or "sandwich" immunometric assay techniques for determination of the presence and/or concentration of antigenic substances in fluids using monoclonal antibodies. One monoclonal antibody is presented in a soluble labeled form and a second monoclonal antibody is presented bound to a solid carrier. The soluble and bound monoclonal antibodies may be the products of either the same or different cell lines. Each monoclonal antibody has an affinity for the antigenic substances of at least about 108 liters/mole.

U.S. Pat. No. 4,435,504 defines a chromatographic immunoassay employing a specific binding pair member and a label conjugate which delineate a border whose distance from one end of the chromatograph relates to the amount of analyte present. By combining the label conjugate and sample in a solution and immunochromatographing the solution, or employing a combination of enzymes, one enzyme being the label and the other enzyme affixed to the chromatographic support, the position of the border defined by the label can be related to the amount of analyte in the sample solution. Preferably, an immunochromatograph is employed having both a specific binding pair member and an enzyme affixed to the support. A sample is chromatographed and the amount of analyte is determined by (1) contacting the chromatograph with a second enzyme conjugated with a specific binding pair member which binds to the chromatograph in proportion to the amount of analyte bound to the chromatograph, or (2) including the second enzyme conjugate with the sample, resulting in a defined border related to the amount of analyte in the sample. The two enzymes are related in that the substrate of one is the product of the other, so that upon contact of the chromatograph with appropriate reagents, a detectable signal develops which permits detection of the border to which the analyte traveled. This distance can be related to the amount of analyte present in the sample.

U.S. Pat. No. 4,703,017 concerns a solid phase assay for an analyte where the binder is supported on a solid support, such as nitrocellulose, and the tracer is comprised of ligand labeled with a colored particulate label, such as a liposome including a dye. The assay has a high sensitivity, and the tracer is visible on the support under assay conditions without instrumentation and without further treatment.

U.S. Pat. No. 4,855,240 consists of a test device and assay for determining an analyte where the tracer and sample may be simultaneously applied to different absorbent material portions both in capillary flow communication with an absorbent material portion. The sample contacts the binder prior to any substantial contact between the sample and tracer or the tracer and binder.

U.S. Pat. No. 4,954,452 describes a method of performing a diagnostic immunoassay utilizing colloidal non-metal particles having conjugated to them a binding component capable of specifically recognizing an analyte to be determined. After reaction of the sample and colloidal non-metal particles, the presence or amount of analyte/colloidal non-metal particle complexes is determined by optical analysis as a measure of the amount of analyte in the sample. The method can be utilized for the specific detection of numerous analytes and is sensitive and has a wide detection range.

U.S. Pat. No. 5,028,535 is directed to a ligand-receptor assay for determining the presence or amount of at least one target ligand capable of competing with a ligand analogue conjugate for binding sites available on a ligand receptor. The ligand analogue conjugate has at least one ligand analogue coupled to a signal development element capable of emitting a detectable signal, in a fluid sample suspected of containing the target ligand. The assay includes the steps of: a. contacting the fluid sample with the ligand analogue conjugate and ligand receptor to form a reaction mixture, the relative amounts of ligand analogue conjugate and ligand receptor being such that in the absence of the target ligand, and subsequent to substantially equilibrium binding, substantially all of the ligand analogue conjugate is bound to the ligand receptor; b. detecting the unbound ligand analogue conjugate; and, c. relating the detectable signal to the presence or amount of target ligand in the fluid sample. In one embodiment, an optional means also is employed for removing the receptor from the reaction mixture. In other assay formats, the analyte of interest may be either a ligand receptor or ligand.

U.S. Pat. No. 5,075,078 shows an improved chromatographic strip binding assay device for determining the presence or amount of an analyte present in a patient sample. Assay label reagents interact with capture reagents immobilized in a testing region on the strip substrate to generate a visually detectable image indicative of the test result. The test result images include a minus sign (−) to indicate a negative test result if the suspect analyte is absent in the patient sample and a plus sign (+) to indicate a positive test result if the suspect analyte is present or is present at a pre-determined concentration in the patient sample. The immobilized capture reagents responsible for the location and configuration of the test result images are applied to the strip at an angled orientation with respect to the fluid flow direction of the strip to ensure that sharp, substantially complete test result images are formed during performance of the assay. The devices are designed to provide substantially self-performing assays having inherently clear test results which are not subject to misinterpretation by the skilled or untrained user.

PCT Application WO 95/16207 is directed to an assay device with a barrier for regulating reagent application. An assay device for detection and/or determination of an analyte in a test sample uses a barrier containing an aperture to control the application of reagents to the device for greater reproducibility of results.

U.K. Patent 2,204,398 pertains to an analytical test device for use in assays. The device is suitable for use in the home, clinic, or doctor's surgery, and is intended to give an analytical result which is rapid and which requires the minimum degree of skill and involvement from the user. In a typical embodiment, the test device comprises a hollow casing containing a dry porous carrier which communicates directly or indirectly with the exterior of the casing such that a liquid test sample can be applied to the porous carrier.

In 1971 Hara et al. first described a protein in the seminal fluid, named gamma-seminoprotein. In 1978, Sensabaugh et al. characterized the protein in detail, found that its molecular weight corresponds to 30,000 Dalton, and named it p30. In 1980, Graves and Sensabaugh described the development of immunometric assays that demonstrated that p30 is a reliable forensic marker for the identification of semen. A range of 200,000 to 5.5 million nanograms of p30 per ml of semen was described. Other methods of detection of p30 have been developed including Ouchterlony double diffusion, crossover electrophoresis, rocket immunoelectrophoresis, radial immunodiffusion, and ELISA. A disadvantage of all these conventional methods is that they are either not sensitive enough or cumbersome and time consuming to perform in forensic laboratories.

DISCLOSURE OF INVENTION

The present invention is directed to a test device of the immunoassay variety which detects the presence of semen. The test device of the present invention overcomes the disadvantages of prior art semen tests, provides accurate results, and can be performed and results available in about 10 minutes or less. The test device can be used in hospitals, sexual assault centers, trauma centers, forensic laboratories, and at field sites. A preferred name is Abacus OneStep ABAcard® p30 Test. The test is sensitive to 4 ng of p30 per ml. Therefore, seminal fluid diluted up to 1 in a million is detectable.

Principle Behind the Test

In this test procedure, 200 μl of sample is added to the sample well "S", and allowed to soak in. If p30 is present in the semen specimen, it will react with the mobile monoclonal antihuman p30 antibody forming a mobile antigen-antibody complex. This mobile antibody-antigen complex migrates through the absorbent device towards the test area "T". A monoclonal antihuman p30 antibody is present in the test area "T". This immobilized antibody captures the above complex so that an antibody-antigen-antibody sandwich is formed. The conjugated pink dye particles concentrate in a narrow zone on the membrane. When the p30 concentration in the sample exceeds 4 ng/ml, the pink dye particles will form a pink colored band in the test area "T" indicating a positive test result. As an internal positive control, p30 antibody-dye conjugates cannot bind to the antibody in the test area "T", but are captured by an immobilized anti immunoglobulin antibody present in the control area "C" forming a complex. The captured pink dye particles will thus form a band in the control area "C" indicating that the test has worked properly and proper procedures have been followed. Thus, the presence of two colored lines, one in the test area "T" and other in the control area "C", indicates a positive result, while a line only in the control area "C" indicates a negative result (provided no "high dose hook effect").

In accordance with a preferred embodiment of the invention, the test device for detecting semen comprises a strip having a test sample introduction station, a test station, and a control station, the stations being disposed in spaced apart relationship along the strip. In a ready for use test device, the test sample introduction station includes labeled p30 antibodies, the test station includes immobilized p30 antibodies, and the control station includes immobilized polyclonal antibodies.

In accordance with another preferred embodiment, the test sample introduction station includes labeled monoclonal p30 antibodies, and the test station includes immobilized monoclonal p30 antibodies.

In accordance with another preferred embodiment, the test station also includes immobilized human IgM antibodies with immobilized human IgM monoclonal antibodies being preferred.

In accordance with a important aspect of the invention, the labeled p30 antibodies have a label selected from the group consisting of colloidal gold, colloidal silver, carbon, latex, dye, and enzyme.

Other features and advantages of the present invention will become apparent from the following detailed description, taken in conjunction with the accompanying drawings, which illustrate, by way of example, the principles of the invention.

BRIEF DESCRIPTION OF DRAWINGS

FIG. 1 is a top plan view of the test device prior to use;

FIG. 2 is a top plan view of the test device after use showing the presence of semen;

FIG. 3 is a top plan view of the test device after use showing no semen present, FIG. 4 is a top plan view of the test device after use showing an invalid test;

FIG. 5 is a top plan view of a test strip portion of the test device for detecting semen in accordance with the present invention;

FIG. 6 is a side elevation view of the test strip;

FIG. 7 is a side elevation view of the test strip showing the substances present at a test sample introduction station after the introduction of a liquid test sample containing semen;

MODES FOR CARRYING OUT THE INVENTION

Figure 8:
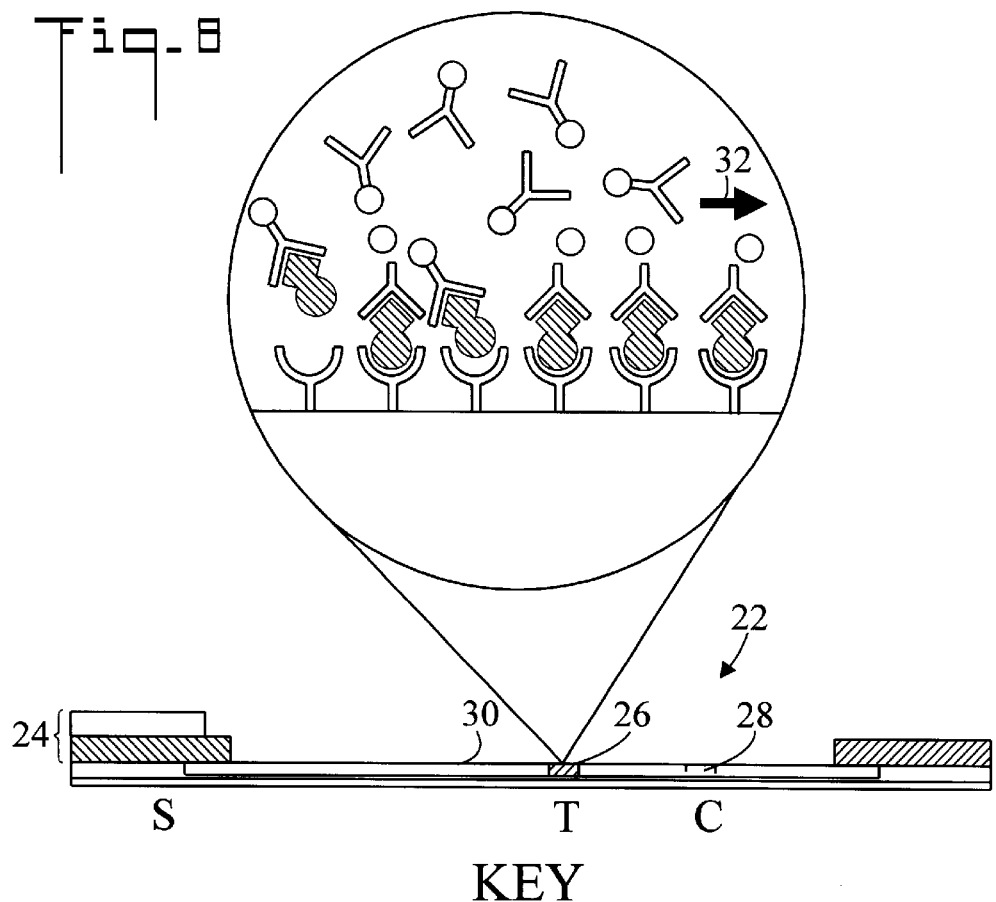
FIG. 8 is a side elevation view of the test strip showing the substances present at the test station after the introduction of a liquid test sample containing semen; and, FIG. 9 is a side elevation view of the test strip showing the substances present at the control station after the introduction of a liquid test sample.

Referring initially to FIG. 1, there is illustrated a test device for detecting semen in accordance with the present invention, generally designated as 20. Test device 20 includes a strip 22 (also refer to FIGS. 5 and 6) having a test sample introduction station 24 ("S"), a test station 26 ("T"), and a control station 28 ("C"), the stations being disposed in spaced apart relationship. Strip 22 is disposed within a housing 23 having apertures for introducing a test sample and viewing the test results. In the figure, test station 26 and control station 28 are shown in dashed lines indicating their location on strip 22. Prior to the test the stations are the same color as the membrane member 30 (FIGS. 5 and 6) which is usually white. A liquid test sample is introduced at test sample introduction station 24 which migrates in all directions including along strip 22 to test station 24 and then to control station 26. FIG. 2 is a top plan view of test device 20 after use showing the presence of semen. If semen is present in the test sample, a colored line (indicated by a hashed area) has appeared at both test station 26 and control station 28. FIG. 3 is a top plan view of test device 20 after use showing no semen present. If there is no semen present in the test sample, no colored line appears at test station 26, but a colored line does appear at control station 28. FIG. 4 is a top plan view of test device 20 after use showing an invalid test. The fact that no colored line appears at control station 28 dictates that the test was inconclusive and should be repeated using another test device 20.

FIGS. 5 and 6 illustrate top plan and side elevation views, respectively, of the strip 22 portion of test device 20. In a prefered embodiment, test sample introduction station 24 includes a sample pad 25 and a conjugate pad 27. Sample pad 25 is disposed above conjugate pad 27, distributes a test sample 500 (FIG. 7) over the conjugate pad 27, removes particles from the test sample 500, can adjust the pH or viscosity of the test sample 500, and facilitates the release of the detector reagent. Strip 22 comprises an elongated membrane member 30 which both absorbs and promotes migration of a test sample 500. In a preferred embodiment, membrane member 30 is made of nitrocellulose and is usually white. Test sample 500 is introduced at test sample introduction station 24, sample pad and conjugate pad, and migrates along membrane member 30, first to test station 26, then to control station 28, and lastly to an absorbent pad 36. On strip 22, test introduction station 24, test station, 26, and control station 28 are disposed in spaced apart relationship.

FIG. 7 illustrates a side elevation view of strip 22 showing the substances present at test sample introduction station 24 after the introduction of a liquid test sample 500 containing semen having the p30 antigen. In usual practice, a test sample 500 is diluted with distilled water, or buffers such as PBS or HEPES. At the test sample introduction station, mobile labeled p30 antibodies are present on the conjugate pad 27 having the label loosely bonded to the p30 antibody forming a conjugate. In a preferred embodiment the labeled p30 antibodies are labeled monoclonal p30 antibodies. The label, which provides a visual indication of a positive result, is selected from the group consisting of colloidal gold, colloidal silver, carbon, latex, dye, and enzyme. When a test sample 500 containing the p30 antigen is deposited, some of the p30 antigen binds to the labeled p30 conjugate forming a complex, while other labeled p30 conjugate remains unbound. Both the bound and unbound labeled p30 antibodies migrate in direction 32 along membrane member 30 toward test station 26.

FIG. 8 is a side elevation view of strip 22 showing the substances present at test station 26 after the mixture has reached the test station. Test station 26 has immobilized p30 antibodies. In a preferred embodiment, the immobilized p30 antibodies are immobilized monoclonal p30 antibodies. In another preferred embodiment, immobilized human IgM antibodies are also present at test station 26. The combination of immobilized monoclonal p30 antibodies and immobilized monoclonal human IgM antibodies results in better blocking and more specific test results. At the test station 26, the labeled antibody/antigen complexes arriving from the test sample introduction site 24 bind with the immobilized p30 antibodies to form a sandwich. In the process, the label is released providing a visual indication, in the form of a colored line, that the semen p30 antigen is present in the test sample 500. The unbound labeled monoclonal p30 antibodies continue to migrate along membrane 30 in direction 32 toward control station 28.

Figure 9:
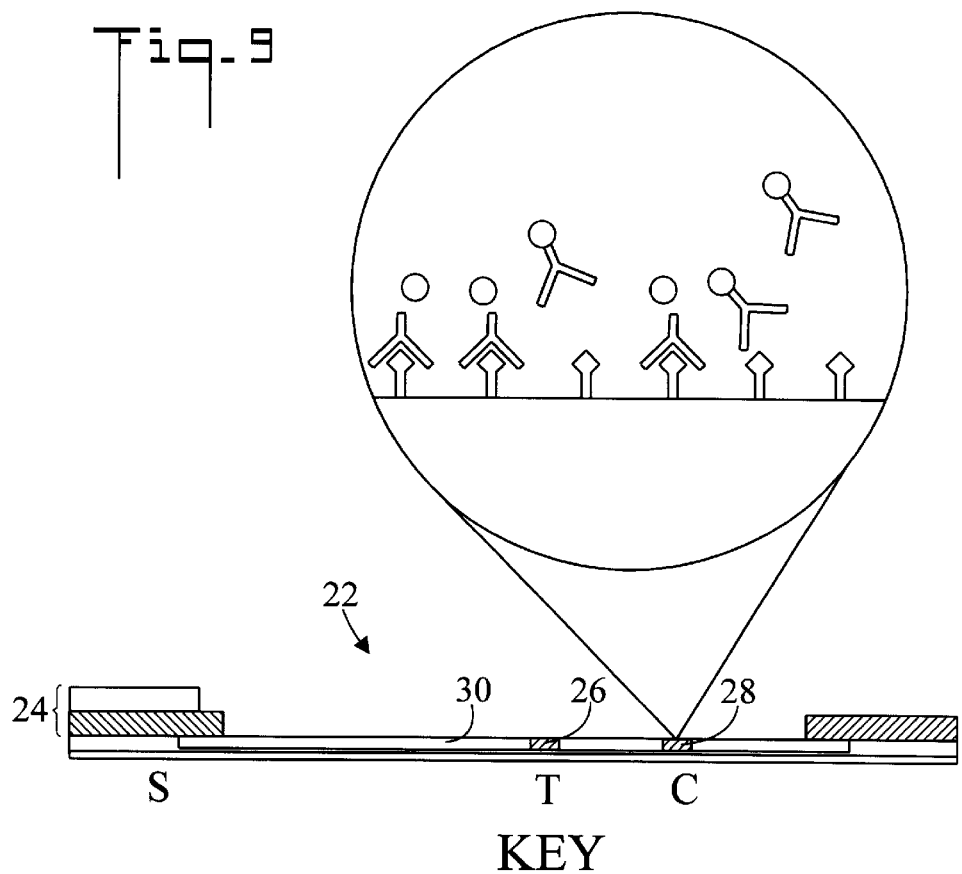

FIG. 9 is a side elevation view of strip 22 showing the substances present at control station 28 when the mixture reaches the control station. Control station 28 has immobilized polyclonal antibodies. Labeled p30 antibodies arriving at control station 28 from test station 26 bind with the immobilized polyclonal antibodies thereby releasing the label and providing a colored line. The colored line is created whether the original test sample 500 did or did not contain the semen p30 antigen. It serves merely to show that enough of the sample was deposited to wet the entire strip 22 including the area of the control station 28.

In a preferred embodiment, the following concentrations have been found useful for a test device 20: 1. at the test sample introduction station 24, two micrograms of labeled monoclonal p30 antibodies; 2. at the test station 26, five micrograms of immobilized monoclonal p30 antibodies and two micrograms of immobilized human IgM antibodies; and, 3. at the control station 28, five micrograms of immobilized polyclonal antibodies.

Additionally, in a preferred embodiment, a protein stabilizer such as bovine serum albumin in an amount of 1 microgram per test device 20 is used. Also, a preservative such as sodium azide is used in an amount of 0.1 microgram per test device 20. And, two buffers have been found to be useful: SDB in an amount of 0.025 micrograms per test device 20, and SALTO in an amount of 0.085 micrograms per test device 20.

One method for determining the presence of semen using the present invention includes the following steps:

1. providing a test device 20 including a strip 22 having a test sample introduction station 24 having labeled p30 antibodies, a test station 26 having immobilized p30 antibodies, and a control station 28 having immobilized polyclonal antibodies, with the stations disposed in a spaced apart relationship;

2. depositing a test sample 500 containing p30 antigen at the test sample introduction site 24;

3. allowing: the p30 antigen to bind with some of the labeled p30 antibodies to form a complex and both the complex and unbound labeled p30 antibodies to migrate to the test station 26; at the test station 26, the complex to bind with the immobilized p30 antibodies thereby providing a visual indication; the unbound labeled p30 antibodies to migrate to the control station 28; and, at the control station, the unbound labeled p30 antibodies to bind with the immobilized polyclonal antibodies thereby providing a visual indication; and, 4. observing the visual indications at the test and control stations.

In a preferred embodiment, human IgM antibodies are also disposed at test station 26. The method can be performed and test results available in about 10 minutes.

The method may also be used for determining a lack of presence of semen including the following steps:

1. providing a test device 20 which includes a strip 22 having a test sample introduction station 24 having labeled p30 antibodies, a test station 26 having immobilized p30 antibodies, and a control station 28 having immobilized polyclonal antibodies, the stations disposed in spaced apart relationship;

2. depositing a test sample 500 containing no p30 antigen at the test sample introduction site 24;

3. allowing: unbound labeled p30 antibodies to migrate to the test station 26; at the test station 26, no reaction taking place and no visual indication being present; the unbound labeled p30 antibodies migrating to the control station 28; and, at the control station 28, the unbound labeled p30 antibodies to bind with the immobilized polyclonal antibodies thereby providing a visual indication; and, 4. observing the lack of a visual indication at the test station and the presence of a visual indication at the control station.

It is noted that polyclonal p30 antibodies could also be used at the test sample introduction station 24 and test station 26. However, poorer sensitivity, higher background, and lower specificity would result.

It is further noted that the present invention will give a positive test result for any primate semen, but not for the semen of any other species of animals.

Test Protocol

The test device is sealed in a test pouch with a desiccant to prolong the shelf life. A clock or timer is needed for timing the test and a centrifuge is need to concentrate the sample. Any frozen specimens, swabs, or stains must be thawed completely and brought to 2–8° C. Extraction of specimens from a swab or stain may be performed in 750 mL of HEPES buffered saline for 2 hours at 2–8° C. Distilled water or other buffers suitable for further DNA (deoxyribonucleic acid) extraction may be used as well. This procedure recovers approximately 99% of the extractable p30 on the swab. The sample is centrifuged 3 minutes after the above extraction step to concentrate the specimen. A sample of 300 ml of supernatant is removed for testing purposes. This aliquot may be stored at 2–8° C. if not used immediately. Before use in the test device 20, the sample should be brought back to room temperature. Any remaining sample may be used for further DNA analysis without affecting the DNA yield. Eight drops from the dropper or 200 $\mu$L of the sample are deposited in the test sample introduction station 24. The results are ideally read at 10 minutes. Positive results can be seen as soon as 1 minute after deposit depending upon the concentration of p30. If negative results are indicated, no decision should be made until after the full 10 minutes have passed to confirm the result. Specimens with the lowest concentration of p30 take the longest time to react. The results should not be read after 10 minutes since non-specific reactions may occur and may result in false positives.

If there are two pink lines, one each in the test station 26 and the control station 28, the test result is positive and indicates that the p30 level is at or above 4 ng/ml. If there is only one pink line in the control station 28, the test result is negative. This may indicate that no p30 is present above 4 ng/ml or the presence of a "high dose hook effect."

A "high dose hook effect" occurs when the p30 concentration is too high since the text device is very sensitive. When abundant human p30 is available, some binds to the antibody to form the antigen-antibody complex and some is free to migrate towards the test station 26. The antibody in the test station 26 is blocked by this free p30. Therefore the mobile antigen-antibody complex with the pink color cannot bind to the antibody. As a result no pink line will form in the test station 26 although a lot of p30 is present in the sample thereby giving a false negative result. If there is no pink line in the control station 28, the test is inconclusive. If an elevated p30 level is suspected but a negative result is obtained, the test should be repeated with a fresh specimen. For example, an undiluted sample of seminal fluid will produce a "high dose hook effect." It should be retested using a 10 to 10,000 dilution.

Specificity

Hemoglobin (10 g/L), bilirubin (100 mg/L) and lipemic samples, as indicated by triglyceride (5 g/L), do not interfere with the test results. High protein concentration such as prostatic acid phosphatase (1000 ng/ml), albumin (20 g/L), chorionic gonadotropin (900 IU/ml), transferrin (5 g/L) and prolactin (1 mg/L) do not interfere with the test results. The test does not detect p30 in any samples from women. Besides semen from both normal and vasectomized men, positive results were only obtained from post-ejaculate urine and male urine from adult men, when the urine samples were directly added to the test. It is well established that p30 does occur in these male urine samples with a reported mean value of 260 ng/ml. Seminal vesicle specific antigen should not be present when this test is used with urine. Use of another appropriate test is recommended when male urine is in question.

Intra Assay and Inter Assay Studies

Intra-Assay

An intra assay variability study was performed. Ten replicates of known positive and negative p30 samples were tested. The results demonstrated a 100% agreement with the expected results.

Inter-Assay

Independent assays were performed on the above samples with three lots of the test device over a three month period. The assay results were 100% in agreement with the expected results.

The preferred embodiments of the invention described herein are exemplary and numerous modifications, dimensional variations, and rearrangements can be readily envisioned to achieve an equivalent result, all of which are intended to be embraced within the scope of the appended claims.

I claim:

1. A method for determining the presence of semen, comprising:

providing a test device including a strip having a test sample introduction station, a test station, and a control station, said stations disposed in spaced apart relationship, said test sample introduction station including labeled p30 antibodies, said test station including immobilized p30 antibodies and human IgM antibodies, and said control station including immobilized polyclonal antibodies;

depositing a test sample containing p30 antigen at said test sample introduction site;

allowing: said p30 antigen to bind with some of said labeled p30 antibodies to form a complex, both said complex and unbound labeled p30 antibodies migrating to said test station; at said test station, said complex to bind with said immobilized p30 antibodies thereby providing a visual indication; and, said unbound labeled p30 antibodies to migrate to said control station; and, at said control station, said unbound labeled p30 antibodies to bind with said immobilized polyclonal antibodies thereby providing a visual indication; and, observing said visual indications at both said test station and said control station, thereby confirming the presence of semen.

2. The method according to claim 1, further including:

taking about 10 minutes or less to perform said method.

* * * * *